(12) United States Patent
Lee

(10) Patent No.: US 7,964,417 B2
(45) Date of Patent: Jun. 21, 2011

(54) METHOD OF MEASURING DEGREE OF CRYSTALLINITY OF POLYCRYSTALLINE SILICON SUBSTRATE, METHOD OF FABRICATING ORGANIC LIGHT EMITTING DISPLAY USING THE SAME, AND ORGANIC LIGHT EMITTING DISPLAY FABRICATED USING THE SAME

(75) Inventor: Hong-Ro Lee, Yongin-si (KR)

(73) Assignee: Samsung Mobile Display Co., Ltd., Youngin (KR)

( * ) Notice: Subject to any disclaimer, the term of this patent is extended or adjusted under 35 U.S.C. 154(b) by 1022 days.

(21) Appl. No.: 11/593,090

(22) Filed: Nov. 6, 2006

(65) Prior Publication Data

US 2008/0121891 A1    May 29, 2008

(30) Foreign Application Priority Data

Sep. 26, 2006    (KR) .................. 10-2006-0093435

(51) Int. Cl.
*H01L 21/00* (2006.01)
(52) U.S. Cl. ................. 438/7; 438/17; 356/30; 356/301
(58) Field of Classification Search ................ 438/7, 17; 356/30, 301
See application file for complete search history.

(56) References Cited

U.S. PATENT DOCUMENTS

| | | | |
|---|---|---|---|
| 5,389,580 A * | 2/1995 | Miyasaka | ............ 438/479 |
| 5,455,673 A | 10/1995 | Alsmeyer et al. | |
| 7,563,659 B2 | 7/2009 | Kwon et al. | |
| 2001/0002324 A1 * | 5/2001 | Maekawa et al. | ............ 438/157 |
| 2003/0232468 A1 | 12/2003 | Ohnuma | |

FOREIGN PATENT DOCUMENTS

| | | |
|---|---|---|
| JP | 62-145775 | 6/1987 |
| JP | 10-107106 | 4/1998 |
| JP | 2002-9012 | 1/2002 |
| JP | 2002-231631 | 8/2002 |
| JP | 2006-66607 | 3/2006 |
| KR | 10-2005-0054788 | 6/2005 |
| KR | 10-2005-0076238 | 7/2005 |
| KR | 10-2005-0106547 | 11/2005 |
| KR | 10-2005-0111169 | 11/2005 |

OTHER PUBLICATIONS

Office Action issued in corresponding European Patent Application No. 06256561.9 dated Oct. 6, 2008.
K. Girotra et al., "70.4: A 14.1inch AMOLED Display using Highly Stable PECVD based Microcrystalline Silicon TFT Backplane" SID 2006, 2006 SID International Symposium, Society for Information Display, LO, vol. XXXVII, May 24, 2005, pp. 1972-19751.

(Continued)

*Primary Examiner* — Matthew S Smith
*Assistant Examiner* — John M Parker
(74) *Attorney, Agent, or Firm* — H.C. Park & Associates, PLC

(57) ABSTRACT

A method of measuring a degree of crystallinity of a polycrystalline silicon substrate includes obtaining a Raman spectrum graph by irradiating a polycrystalline silicon substrate with a laser beam; and calculating a degree of crystallinity of the polycrystalline silicon substrate from the Raman spectrum graph using the following formula: (degree of crystallinity)=(area of polycrystalline peak)/[(area of amorphous peak)+(area of polycrystalline peak)].

10 Claims, 9 Drawing Sheets

OTHER PUBLICATIONS

Database Inspec [Online] The Institution of Electrical Engineers, Stevenage, GB; 2003, Xu Xiao-Xuan et al: "Raman depth profile research of laser crystallized a; Si film"; XP002495499 Database accession No. 7784387 & Chinese Journal of Luminescence Science Press China, vol. 24, No. 4, 2003, pp. 426-430.

Z. Iqbal et al., "Raman scattering from small particle size polycrystalline silicon" Solid State Communications USA, vol. 37, No. 12, Mar. 1981, pp. 993-996.

K. Chung et al., "70.1: Invited Paper: Large-Sized Full Color AMOLED TV: Advancements and Issues," SID 2006, 2006 SID International Symposium, Society for Information Display, LO, vol. XXXVII, May 24, 2005, pp. 1958-1963.

S. Toshiharu, "Flat panel displays for ubiquitous product applications and related impurity doping technologies" Journal of Applied Physics, American Institute of Physics. New Yokr, US, vol. 99, No. 11, Jun. 1, 2006, pp. 111101-1-111101-15.

Z. Iqbal et al., "Raman Scattering from Small Particle Size Polycrystalline Silicon," *Solid State Communications*, vol. 37, No. 12, Mar. 1981, pp. 993-996.

X. Xiao-xuan et al. "Raman Depth Profile Research of Laser Crystallized a:Si Film," *Chinese Journal of Luminescence*, vol. 24., No. 4, Aug. 2003, pp. 426-420 (in Chinese with two English abstracts).

K. Chung et al., "70.1: *Invited Paper*: Large-Sized Full Color AMOLED TV: Advancements and Issues," *SID Symposium Digest of Technical Papers*, vol. 37, No. 1, Jun. 2006, pp. 1958-1963, Society for Information Display 2006, International Symposium, Seminar and Exhibition, Jun. 4-9, San Francisco.

K. Girotra et al., "70.4: A 14.1inch AMOLED Display using Highly Stable PECVD based Microcrystalline Silicon TFT Backplane," *SID Symposium Digest of Technical Papers*, vol. 37, No. 1, Jun. 2006, pp. 1972-1975, Society for Information Display 2006, International Symposium, Seminar and Exhibition, Jun. 4-9, San Francisco.

T. Suzuki, Flat panel displays for ubiquitous product applications and related impurity doping technologies, *Journal of Applied Physics*, vol. 99, No. 11, Jun. 1, 2006, pp. 111101-1-111101-15.

Extended European Search Report issued on Oct. 6, 2008, in European Patent Application No. 06256561.9 (11 pages, in English).

Xiao-Dan, Zhang, et al. "A Study of Raman and Optical Emission Spectroscopy on Microcrystalline Silicon Films Deposited by VHF-PECVD." *Acta Physica Sinica*. vol. 54. pp. 445-449. Jan. 31, 2005. (In Chinese, with English Abstract).

Xiangbin, Zeng, et al. "Preparation of Polycrystalline Films and TFT by EF-MILC (Electric-field Enhanced Metal-Induced Lateral Crystallization)." *Functional Materials*. 2004.

Office Action issued by the Japanese Patent Office on Apr. 7, 2009.

Office Action issued by the Chinese Patent Office on Apr. 10, 2009.

Z. Xiangbin et al., "Preparation of Polycrystalline films and TFT by EF-MILC (Electric-field Enhanced Metal-Induced Lateral Crystallization)," *Journal of Functional Materials*, vol. 35, magazine supplement, Dec. 31, 2004, pp. 1172-1175 (4 pages, in Chinese, no English abstract or translation).

Z. Xiao-Dan et al., "A study of Raman and optical emission spectroscopy on microcrystalline silicon films deposited by VHF-PECVD," *Acta Physica Sinica*, vol. 54, No. 1, Jan. 2005, pp. 445-449 (5 pages, in Chinese with English abstract).

Japanese Office Action issued on Apr. 7, 2009, in Japanese Application No. 2006-277283 (3 pages, in Japanese, no English translation).

Chinese Office Action issued on Apr. 10, 2009, in Chinese Application No. 2006101628780 (17 pages, in Chinese with complete English translation of text of Chinese Office Action).

\* cited by examiner

METHOD OF MEASURING DEGREE OF CRYSTALLINITY OF POLYCRYSTALLINE SILICON SUBSTRATE, METHOD OF FABRICATING ORGANIC LIGHT EMITTING DISPLAY USING THE SAME, AND ORGANIC LIGHT EMITTING DISPLAY FABRICATED USING THE SAME

CROSS-REFERENCE TO RELATED APPLICATION

This application claims the benefit of Korean Patent Application No. 2006-93435 filed on Sep. 26, 2006, in the Korean Intellectual Property Office, the disclosure of which is incorporated herein by reference in its entirety.

BACKGROUND OF THE INVENTION

1. Field of the Invention

An aspect of the invention relates to a method of measuring a degree of crystallinity of a polycrystalline silicon substrate, a method of fabricating an organic light emitting display using the same, and an organic light emitting display fabricated using the same, and, more particularly, to a method of measuring a degree of crystallinity of a polycrystalline silicon substrate using a Raman spectrum graph, a method of fabricating an organic light emitting display using the same, and an organic light emitting display fabricated using the same.

2. Description of the Related Art

Since polycrystalline silicon has a high mobility compared to amorphous silicon (a-Si for short), polycrystalline silicon is used in various electronic devices such as solar cells and flat panel displays.

The mobility of polycrystalline silicon is related to a degree of crystallinity of the polycrystalline silicon. Methods of estimating the degree of crystallinity may include a Raman spectroscopic analysis method.

When a transparent material is irradiated with an intense monochromatic light and the spectrum of light scattered from the transparent material is analyzed, spectral lines having a longer or shorter wavelength than the wavelength of the incident light are observed in addition to a spectral line having the wavelength of the incident light. This phenomenon is known as the Raman effect. A Raman spectroscopic analysis method uses the Raman effect.

In general, the degree of crystallinity of the polycrystalline silicon is estimated based on a full width at half maximum (FWHM) of a Raman spectrum graph. Specifically, as the FWHM of the Raman spectrum graph decreases, the degree of crystallinity of the polycrystalline silicon increases.

However, the method of measuring the degree of crystallinity based on the FWHM of the Raman spectrum graph has a problem in that the method tends to be unreliable.

In addition, the aforementioned method of measuring the degree of crystallinity has a problem in that the method does not consider the dispersion of a threshold voltage (Vth) that is an important characteristic of a thin film transistor.

SUMMARY OF THE INVENTION

Several aspects and example embodiments of the invention provide a more reliable method of measuring a degree of crystallinity of a polycrystalline silicon substrate.

In addition, the invention provides an organic light emitting display having excellent electrical characteristics such as mobility and threshold voltage dispersion, and a method of fabricating the same.

According to an aspect of the invention, a method of measuring a degree of crystallinity of a polycrystalline silicon substrate includes obtaining a Raman spectrum graph by irradiating a polycrystalline silicon substrate with monochromatic light; and calculating a degree of crystallinity of the polycrystalline silicon substrate from the Raman spectrum graph using the following formula: (degree of crystallinity)=(area of polycrystalline peak)/[(area of amorphous peak)+(area of polycrystalline peak)].

According to an aspect of the invention, the calculating of the degree of crystallinity of the polycrystalline silicon substrate may include deconvolving the Raman spectrum graph into the amorphous peak and the polycrystalline peak; calculating the area of the amorphous peak and the area of the polycrystalline peak from data obtained during the deconvolving of the Raman spectrum graph; and calculating the degree of crystallinity using the calculated area of the amorphous peak and the calculated area of the polycrystalline peak in the formula.

According to an aspect of the invention, the amorphous peak may have a center at 480 $cm^{-1}$, and the polycrystalline peak may have a center at 517 $cm^{-1}$.

According to an aspect of the invention, a method of fabricating an organic light emitting display includes fabricating a polycrystalline silicon substrate by crystallizing an amorphous silicon substrate; obtaining a Raman spectrum graph by irradiating the polycrystalline silicon substrate with monochromatic light; examining a degree of crystallinity of the polycrystalline silicon substrate based on the Raman spectrum graph by using the following formula: (degree of crystallinity)=(area of polycrystalline peak)/[(area of amorphous peak)+(area of polycrystalline peak)]; and fabricating a thin film transistor using the polycrystalline silicon substrate depending on a result of the examining of the degree of crystallinity of the polycrystalline silicon substrate.

According to an aspect of the invention, the fabricating of the polycrystalline silicon substrate may include crystallizing the amorphous silicon substrate using a solid phase crystallization (SPC) method, an excimer laser annealing (ELA) method, a metal induced crystallization (MIC) method, a metal induced lateral crystallization (MILC) method, or a sequential lateral solidification (SLS) method.

According to an aspect of the invention, the fabricating of the thin film transistor may be performed only if the degree of crystallinity of the polycrystalline silicon substrate is determined to be 70% or more in the examining of the degree of crystallinity of the polycrystalline silicon substrate.

Additional aspects and/or advantages of the invention will be set forth in part in the description which follows and, in part, will be obvious from the description, or may be learned by practice of the invention.

BRIEF DESCRIPTION OF THE DRAWINGS

The above and/or other aspects and advantages of the invention will become apparent and more readily appreciated from the following description of example embodiments, taken in conjunction with the accompanying drawings of which.

DETAILED DESCRIPTION OF THE EMBODIMENTS

Reference will now be made in detail to example embodiments of the invention, examples of which are shown in the accompanying drawings, wherein like references numerals refer to the like elements throughout. The example embodiments are described below in order to explain the invention by referring to the figures.

Figure 1:
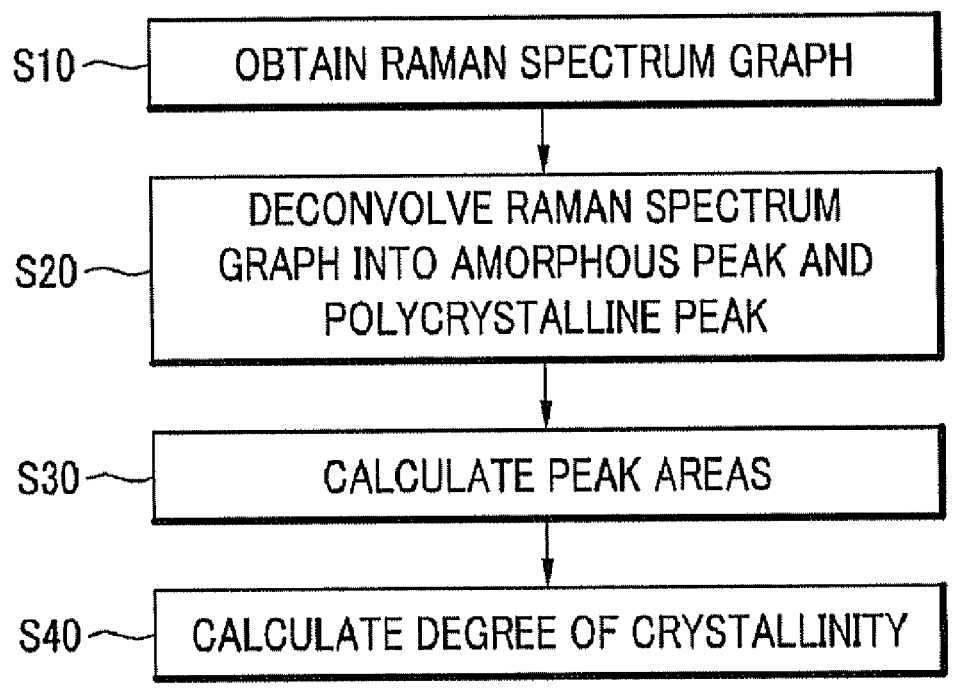
FIG. 1 is a flowchart of a method of measuring a degree of crystallinity of a polycrystalline silicon substrate according to an example embodiment of the invention.

FIG. 1 is a flowchart of a method of measuring a degree of crystallinity of a polycrystalline silicon substrate according to an example embodiment of the invention.

As shown in FIG. 1, the method of measuring the degree of crystallinity of the polycrystalline silicon substrate according to the example embodiment of the invention comprises obtaining a Raman spectrum graph by irradiating the polycrystalline silicon substrate with monochromatic light, such as a laser beam or any other suitable monochromatic light, at block S10; deconvolving the Raman spectrum graph into an amorphous peak and a polycrystalline peak at block S20; calculating an area of the amorphous peak and an area of the polycrystalline peak from data obtained during the deconvolving of the Raman spectrum graph at block S30; and calculating the degree of crystallinity of the polycrystalline silicon substrate using the calculated area of the amorphous peak and the area of the polycrystalline peak according to the following Formula 1 at block S40:

(degree of crystallinity)=(area of polycrystalline peak)/[(area of amorphous peak)+(area of polycrystalline peak)]   Formula 1

The amorphous peak has a center at 480 cm$^{-1}$, and the polycrystalline peak has a center at 517 cm$^{-1}$.

Figure 2:
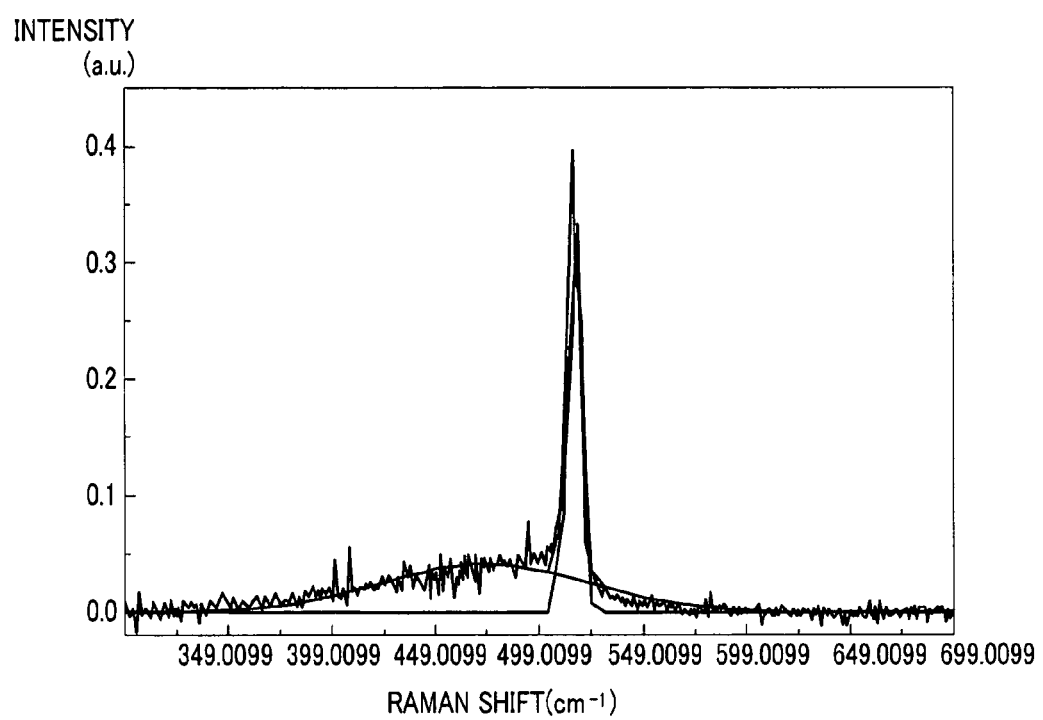
FIG. 2 is a Raman spectrum graph of a polycrystalline silicon substrate having a degree of crystallinity of 32.8%.
Figure 3:
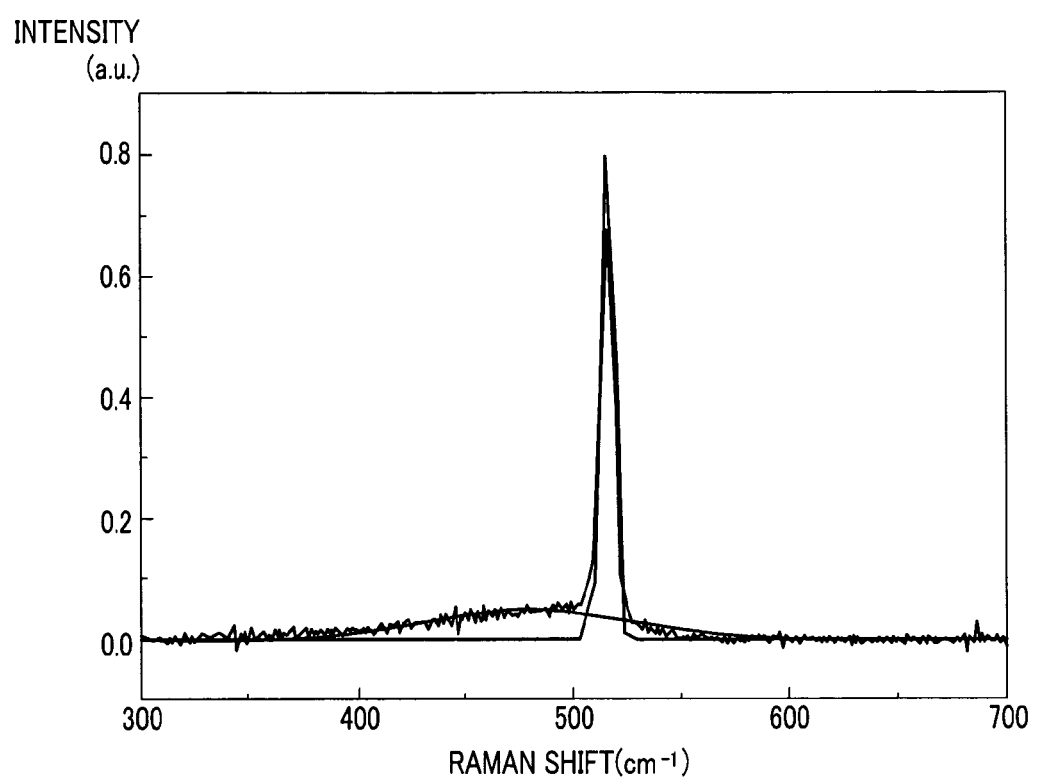
FIG. 3 is a Raman spectrum graph of a polycrystalline silicon substrate having a degree of crystallinity of 49.7%.
Figure 4:
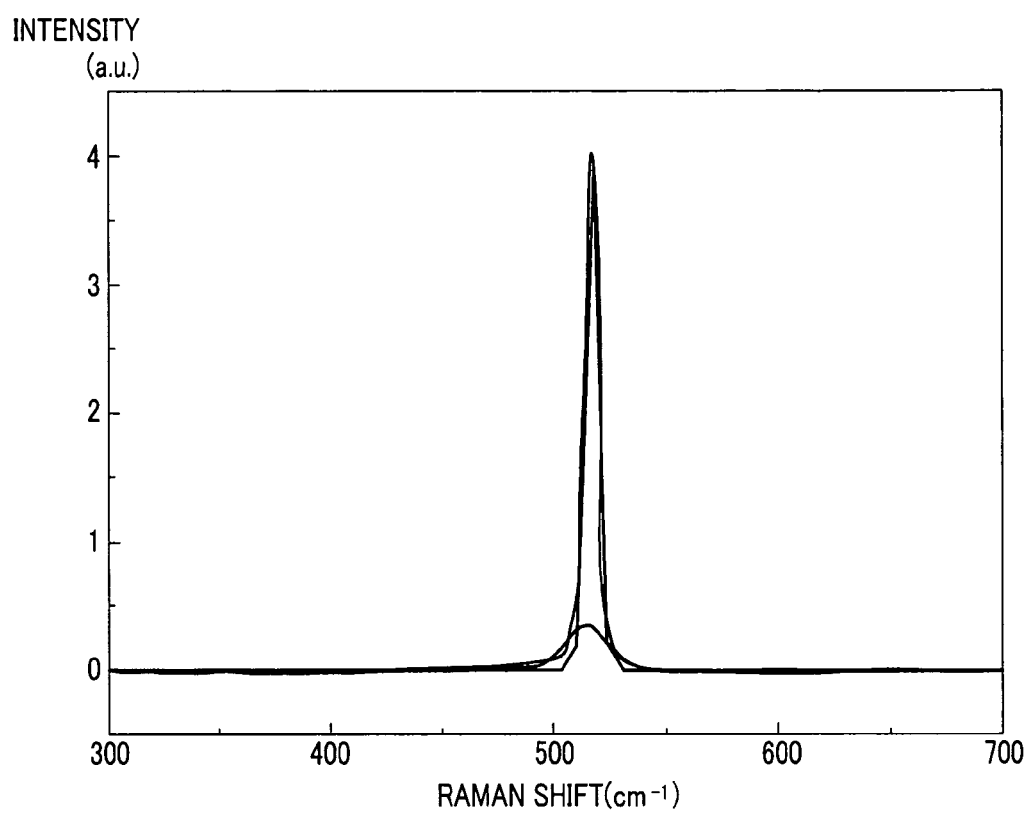
FIG. 4 is a Raman spectrum graph of a polycrystalline silicon substrate having a degree of crystallinity of 75.5%.

FIGS. 2 to 4 are Raman spectrum graphs of polycrystalline silicon substrates having different degrees of crystallinity. As can be seen from FIGS. 2 to 4, each of these Raman spectrum graphs has a different FWHM.

Using the aforementioned method, the degree of crystallinity is measured to be 32.8% from the Raman spectrum graph of FIG. 2, the degree of crystallinity is measured to be 49.7% from the Raman spectrum graph of FIG. 3, and the degree of crystallinity is measured to be 75.5% from the Raman spectrum graph of FIG. 4.

Figure 5:
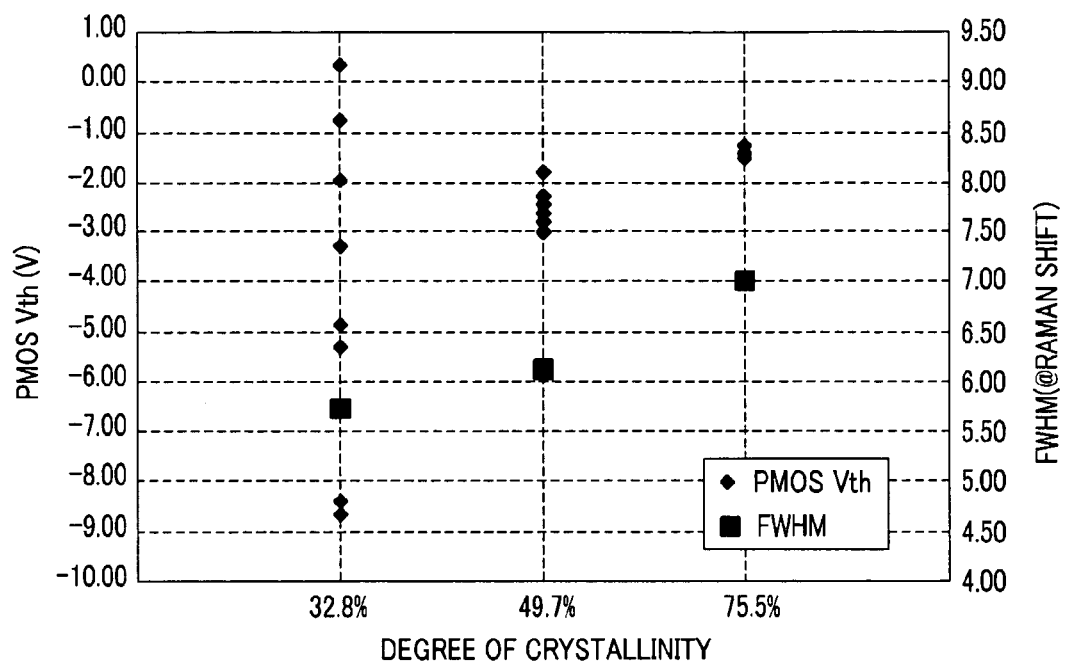
FIG. 5 is a graph of a PMOS threshold voltage and a full width at half maximum (FWHM) of a Raman spectrum graph according to a degree of crystallinity.

FIG. 5 is a graph of a PMOS threshold voltage and a full width at half maximum (FWHM) of a Raman spectrum graph according to a degree of crystallinity of the polycrystalline substrate. As can be seen from FIG. 5, as the degree of crystallinity increases, the threshold voltages become less dispersed. However, the FWHM tends to increase as the degree of crystallinity increases.

As described above, there is an apparent correlation between the dispersion of the threshold voltage of the polycrystalline silicon substrate and the degree of crystallinity as measured by the method of measuring the degree of crystallinity according to an example embodiment of the invention.

Figure 6:
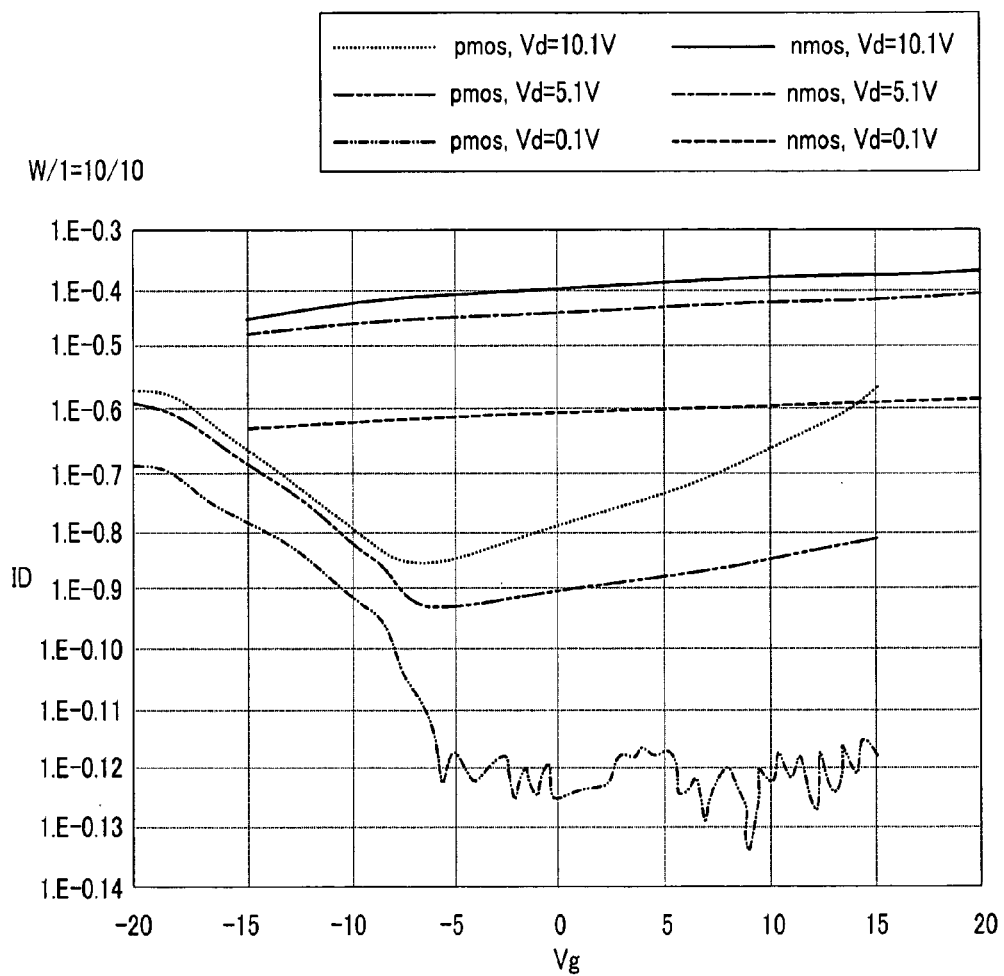
FIG. 6 is a graph of an ID-Vg characteristic of the polycrystalline silicon substrate having the degree of crystallinity of 32.8%.
Figure 7:
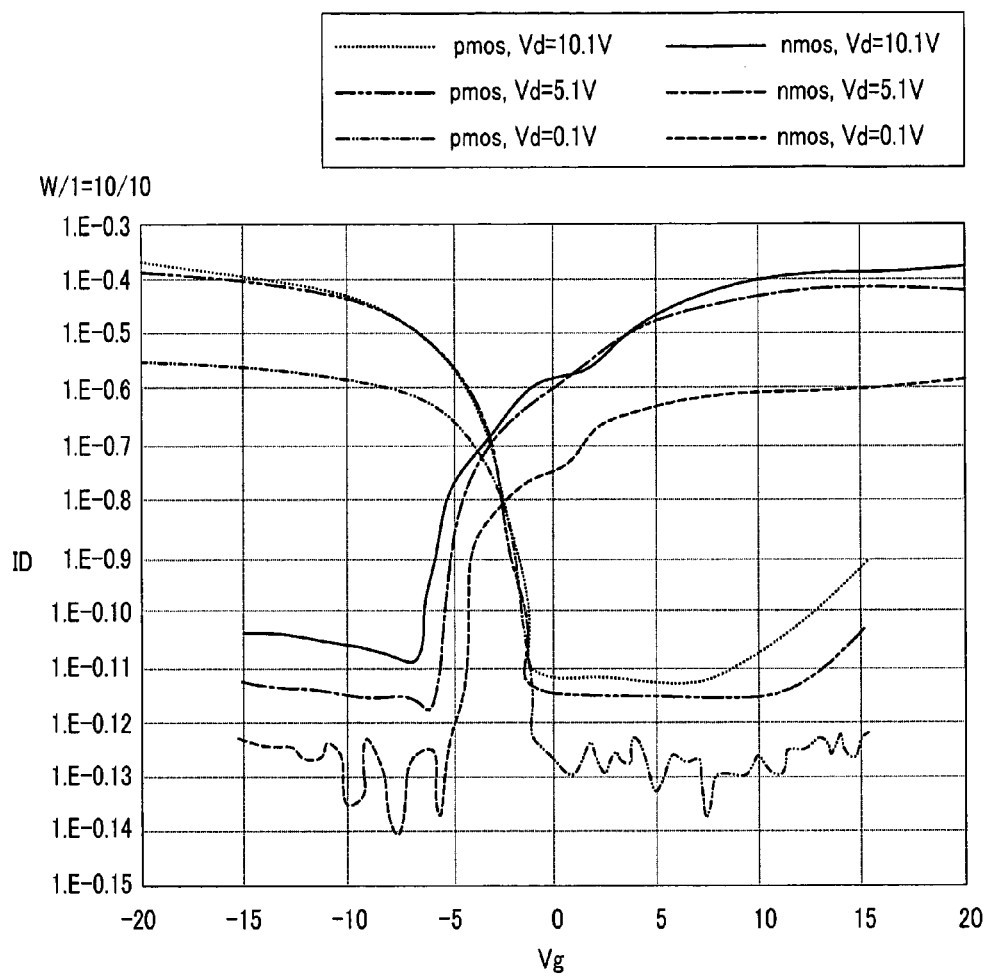
FIG. 7 is a graph of an ID-Vg characteristic of the polycrystalline silicon substrate having the degree of crystallinity of 49.7%.
Figure 8:
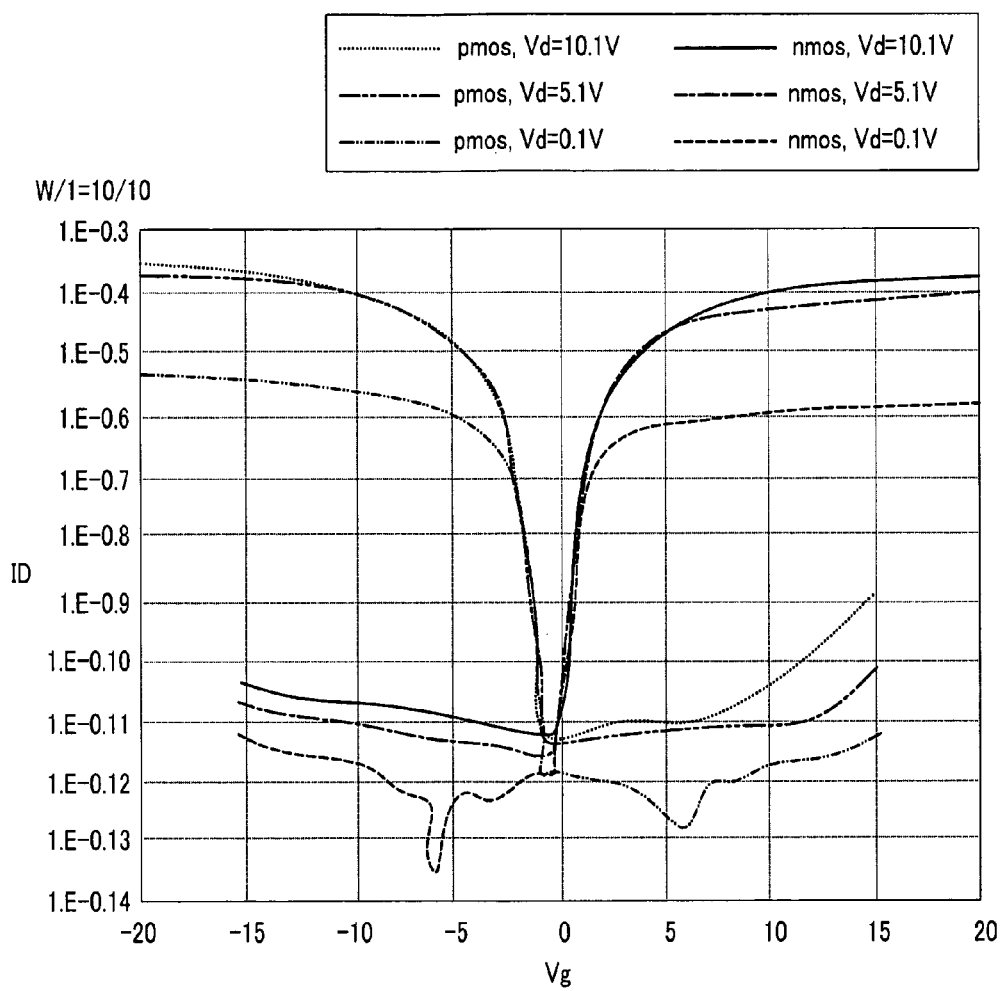
FIG. 8 is a graph of an ID-Vg characteristic of the polycrystalline silicon substrate having the degree of crystallinity of 75.5%.

FIG. 6 is a graph of an ID-Vg characteristic of the polycrystalline silicon substrate having a degree of crystallinity of 32.8%, FIG. 7 is a graph of an ID-Vg characteristic of the polycrystalline silicon substrate having a degree of crystallinity of 49.7%, and FIG. 8 is a graph of an ID-Vg characteristic of the polycrystalline silicon substrate having a degree of crystallinity of 75.5%.

As can be seen from FIGS. 6 to 8, as the degree of crystallinity calculated using Formula 1 increases, that is, when moving from FIG. 6 to FIG. 8, a subthreshold slope decreases, and a kink effect decreases.

This means that a polycrystalline silicon substrate having excellent electrical characteristics such as mobility and threshold voltage dispersion can be obtained.

A method of fabricating an organic light emitting display according to an example embodiment of the invention will now be described.

Figure 9:
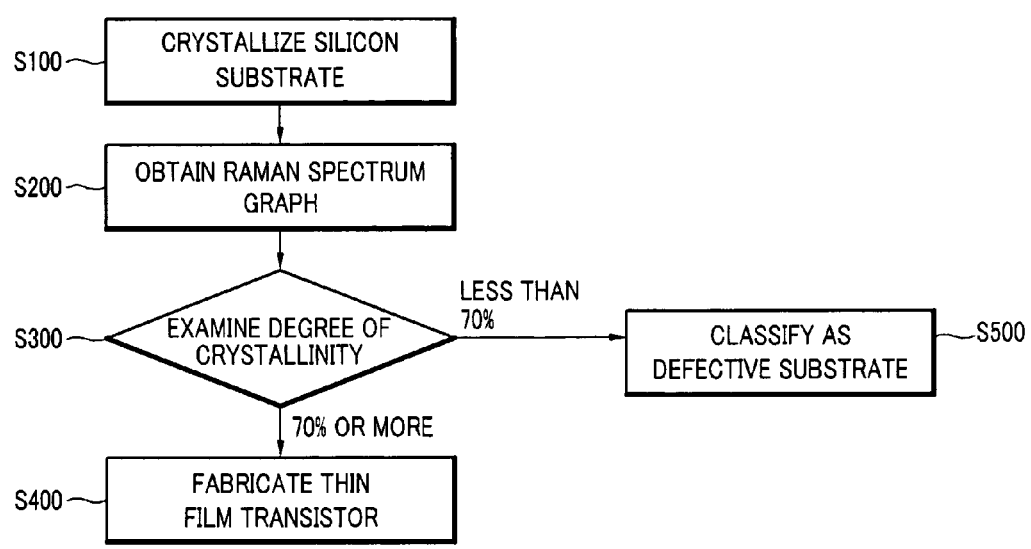
FIG. 9 is a flowchart of a method of fabricating an organic light emitting display according to an example embodiment of the invention.

FIG. 9 is a flowchart of a method of fabricating an organic light emitting display according to an example embodiment of the invention. As shown in FIG. 9, the method of fabricating the organic light emitting display comprises fabricating a polycrystalline silicon substrate by crystallizing an amorphous silicon substrate at block S100; obtaining a Raman spectrum graph by irradiating the polycrystalline silicon substrate with monochromatic light, such as a laser beam or any other suitable monochromatic light, at block S200; examining a degree of crystallinity of the polycrystalline silicon substrate based on the Raman spectrum graph at block S300; and fabricating a thin film transistor at block S400.

The fabricating of the polycrystalline silicon substrate (S100) may be performed using a solid phase crystallization (SPC) method, an excimer laser annealing (ELA) method, a metal induced crystallization (MIC) method, a metal induced lateral crystallization (MILC) method, or a sequential lateral solidification (SLS) method.

The SPC method is a method of crystallizing the amorphous silicon substrate by using a high temperature heat treatment.

The ELA method is a method in which an upper portion of the amorphous silicon substrate is instantaneously melted and recrystallized by irradiating the amorphous silicon substrate with an excimer laser beam.

The MIC method is a method in which a metal catalyst is coated on the amorphous silicon substrate using a sputtering method or a spin coating method to induce crystallization at a low temperature.

The MILC method is a method in which metal seeds are deposited on source and drain regions of the amorphous silicon substrate, and crystallization proceeds laterally in the amorphous silicon substrate away from the metal seeds at a low temperature.

The SLS method is a method in which the amorphous silicon substrate is irradiated with a laser beam two or more times to laterally grow silicon crystal grains to crystallize the amorphous silicon substrate.

The polycrystalline silicon substrate that is crystallized using any of the aforementioned methods is examined during the examination of the degree of crystallinity using the method of measuring the degree of crystallinity of the polycrystalline silicon substrate according to an example embodiment of the invention.

Specifically, a Raman spectrum graph is obtained by irradiating the polycrystalline silicon substrate with monochromatic light, such as a laser beam or any other suitable monochromatic light, at block S200; and the degree of crystallinity of the polycrystalline silicon substrate is examined using the method of measuring the degree of crystallinity according to an example embodiment of the invention at block S300, shown in FIG. 9.

In this case, the thin film transistor used for the organic light emitting display is fabricated using the polycrystalline silicon substrate having a degree of crystallinity that is 70% or more at block S400.

In an active matrix organic light emitting display, the threshold voltage dispersion causing non-homogeneity of luminance is more important than the absolute value of an electrical characteristic such as mobility or threshold voltage.

When the threshold voltage dispersion is 1.0V or more, serious non-homogeneity of the luminance occurs even if a circuit for compensating for the threshold voltage dispersion is used.

Accordingly, the thin film transistor used for the organic light emitting display is fabricated at block S400 using a polycrystalline silicon substrate that is determined to have a degree of crystallinity of 70% or more in the examining of the degree of crystallinity at block S300, while any polycrystalline silicon substrate determined to have a degree of crystallinity of less than 70% is classified as a defective substrate at block S500. However, the invention is not limited to using a degree of crystallinity of 70% as a threshold value at block S300 to determine whether a polycrystalline silicon substrate will be used to fabricate a thin film transistor at block S400, or will be classified as a defective substrate at block 500, and other degrees of crystallinity may be used as a threshold value at block 300 depending on the desired characteristics of the thin film transistor to be fabricated.

As described above, in a method of measuring the degree of crystallinity of the polycrystalline silicon substrate and a method of fabricating the organic light emitting display according to an aspect of the invention, the organic light emitting display having excellent mobility and threshold voltage dispersion characteristics can be provided by using a reliable method of measuring the degree of crystallinity of the polycrystalline silicon substrate.

Although several example embodiments of the invention have been shown and described, it would be appreciated by those skilled in the art that changes may be made in these example embodiments without departing from the principles and spirit of the invention, the scope of which is defined in the claims and their equivalents.

What is claimed is:

1. A method of measuring a degree of crystallinity of a polycrystalline silicon substrate, the method comprising:
    obtaining a Raman spectrum graph by irradiating a polycrystalline silicon substrate with monochromatic light;
    deconvolving the Raman spectrum graph into a peak corresponding to amorphous silicon and having a center at 480 cm$^{-1}$ and a peak corresponding to polycrystalline silicon and having a center at 517 cm$^{-1}$;
    calculating the peak area of the amorphous silicon and the peak area of the polycrystalline silicon from data obtained during the deconvolving of the Raman spectrum graph; and
    calculating a degree of crystallinity of the polycrystalline silicon substrate using the calculated peak area of the amorphous silicon and the calculated peak area of the polycrystalline silicon from the Raman spectrum graph in the following formula:
    (degree of crystallinity)=(peak area of polycrystalline silicon)/[(peak area of amorphous silicon)+(peak area of polycrystalline silicon)].

2. The method of claim 1, wherein the monochromatic light is a laser beam.

3. The method of claim 1, further comprising:
    determining that the polycrystalline silicon substrate is acceptable for use in fabricating a thin film transistor if the calculated degree of crystallinity of the polycrystalline silicon substrate exceeds a predetermined degree of crystallinity; and
    determining that the polycrystalline silicon substrate is not acceptable for use in fabricating a thin film transistor if the calculated degree of crystallinity of the polycrystalline silicon substrate does not exceed the predetermined degree of crystallinity.

4. The method of claim 3, wherein the predetermined degree of crystallinity is 70%.

5. A method of fabricating an organic light emitting display, the method comprising:
    fabricating a polycrystalline silicon substrate by crystallizing an amorphous silicon substrate;
    obtaining a Raman spectrum graph by irradiating the polycrystalline silicon substrate with monochromatic light;
    deconvolving the Raman spectrum graph into a peak corresponding to amorphous silicon and having a center at 480 cm$^{-1}$ and a peak corresponding to polycrystalline silicon and having a center at 517 cm$^{-1}$;
    calculating a peak area of the amorphous silicon and a peak area of the polycrystalline silicon from the data obtained during the deconvolving of the Raman spectrum graph; and
    calculating the degree of crystallinity using the calculated peak area of the amorphous silicon and the calculated peak area of the polycrystalline silicon in the following formula:
    (degree of crystallinity)=(peak area of polycrystalline silicon)/[(peak area of amorphous silicon)+(peak area of polycrystalline silicon)]; and
    fabricating a thin film transistor using the polycrystalline silicon substrate depending on a result of the examining of the degree of crystallinity of the polycrystalline silicon substrate.

6. The method of claim 5, wherein the fabricating of the thin film transistor using the polycrystalline silicon substrate is performed only if the degree of crystallinity of the polycrystalline silicon substrate is determined to be 70% or more in the examining of the degree of crystallinity of the polycrystalline silicon substrate.

7. The method of claim 5, wherein the fabricating of the polycrystalline silicon substrate comprises crystallizing the amorphous silicon substrate using a solid phase crystallization (SPC) method, an excimer laser annealing (ELA) method, a metal induced crystallization (MIC) method, a metal induced lateral crystallization (MILC) method, or a sequential lateral solidification (SLS) method.

8. The method of claim 7, wherein the fabricating of the thin film transistor using the polycrystalline silicon substrate is performed only if the degree of crystallinity of the polycrystalline silicon substrate is determined to be 70% or more in the examining of the degree of crystallinity of the polycrystalline silicon substrate.

9. The method of claim 5, wherein the monochromatic light is a laser beam.

10. The method of claim 5, wherein the fabricating of the thin film transistor using the polycrystalline silicon substrate is performed only if the degree of crystallinity of the polycrystalline silicon substrate is determined to exceed a predetermined degree of crystallinity in the examining of the degree of crystallinity of the polycrystalline silicon substrate.

* * * * *